(12) United States Patent
Rudnick et al.

(10) Patent No.: US 6,394,269 B1
(45) Date of Patent: May 28, 2002

(54) NEEDLE PACKAGE WITH POINT GUARDS

(75) Inventors: James J. Rudnick, Mahwah, NJ (US); Joseph Pergine, Chalfont, PA (US); Lance Stairs, Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/676,861

(22) Filed: Sep. 29, 2000

(51) Int. Cl.⁷ .......................... B65D 85/28; A61B 17/06
(52) U.S. Cl. ...................................... 206/380; 206/63.3
(58) Field of Search ............................... 206/63.3, 365, 206/380–382, 227, 379, 564, 574

(56) References Cited

U.S. PATENT DOCUMENTS

| | | | |
|---|---|---|---|
| 3,951,261 A | | 4/1976 | Mandel et al. |
| 3,951,263 A | * | 4/1976 | Vale .......................... 206/63.3 |
| 4,424,898 A | * | 1/1984 | Thyen et al. .............. 206/63.3 |
| 4,619,364 A | | 10/1986 | Czopor, Jr. |
| 5,024,323 A | * | 6/1991 | Bolton ....................... 206/63.3 |
| 5,099,994 A | * | 3/1992 | Kalinski et al. ........... 206/63.3 |
| 5,322,163 A | | 6/1994 | Foos |
| 5,353,922 A | | 10/1994 | Sinn |
| 5,575,382 A | * | 11/1996 | Sobel et al. ............... 206/63.3 |
| 5,617,952 A | * | 4/1997 | Kranendonk ................ 206/380 |
| 5,704,469 A | * | 1/1998 | Daniele et al. ........... 206/63.3 |
| 5,788,062 A | | 8/1998 | Cerwin et al. |
| 5,788,063 A | | 8/1998 | Van Ness |

* cited by examiner

Primary Examiner—Luan K. Bui

(57) ABSTRACT

A package for holding a pointed object such as a needle, includes a tray with an internal hollow delimited by a bottom surface and a sidewall, with the internal hollow receiving the pointed object therein. A removable support member extends parallel to the bottom surface over said internal hollow and supports a point guard depending therefrom. The point guard is interposed between the sidewall and a point on the pointed object to be held. Preferably, the point guard has a thickness that is impenetrable to the pointed object during shipping. A cover sheet loosely holds the point guard in position and the package can accommodate needles within a range of dimensions.

17 Claims, 3 Drawing Sheets

NEEDLE PACKAGE WITH POINT GUARDS

FIELD OF THE INVENTION

The present invention relates to packages for sterile pointed objects, such as needles, and more particularly to thermoformed blister packages for such objects.

BACKGROUND OF THE INVENTION

Blister packs for needles are well known and used due to their effectiveness and economy. Pointed devices, such as needles, especially heavy ones, can puncture their packaging during shipping and handling. In the case of medical devices, punctures in the packaging renders them non-sterile and the sharply pointed devices can pose a safety hazard. In the past, this problem was attempted to be solved by incorporating snap-fit retainers or undercuts in the blister pack to establish an interference/friction fit to retain the pointed object in place within the pack and prevent punctures. In order to make the snap-fit retainers strong enough to hold needles in place within the pack, they must exert a strong grip on the needle which has to be overcome by the user when the needle is removed from the package. Because the use of snap-fit retainers requires a mechanical interaction between the package and the needle demanding close tolerances, a specific package has to be used with each different size needle. Due to the surface smoothness of the plastic material used in forming blister packs and the surface smoothness of needles, along with the high density of the needles, even a tight fit between the retainer and needle does not insure that the needle will not become dislodged given a sufficiently large shock in a critical direction. A known alternative technology is to use needle caps that are friction fit over the point of the needles before packaging to prevent the points from puncturing the packaging during shipping and handling. Protective caps, however, are difficult to remove and complicate time-critical surgical procedures.

SUMMARY OF THE INVENTION

The problems and disadvantages associated with the conventional techniques and devices utilized to hold pointed objects are overcome by the present invention which includes a package having a tray portion with an internal hollow delimited by a bottom surface and a sidewall. The internal hollow receives the pointed object therein and a removable support member extends substantially parallel to the bottom surface over the internal hollow. A point guard depends from the support member towards the tray proximate the sidewall, with the point guard interposable between the sidewall and a point on the pointed object to be held.

BRIEF DESCRIPTION OF THE FIGURES

For a better understanding of the present invention, reference is made to the following detailed description of an exemplary embodiment considered in conjunction with the accompanying drawings, in which.

DETAILED DESCRIPTION OF THE FIGURES

Figure 1:
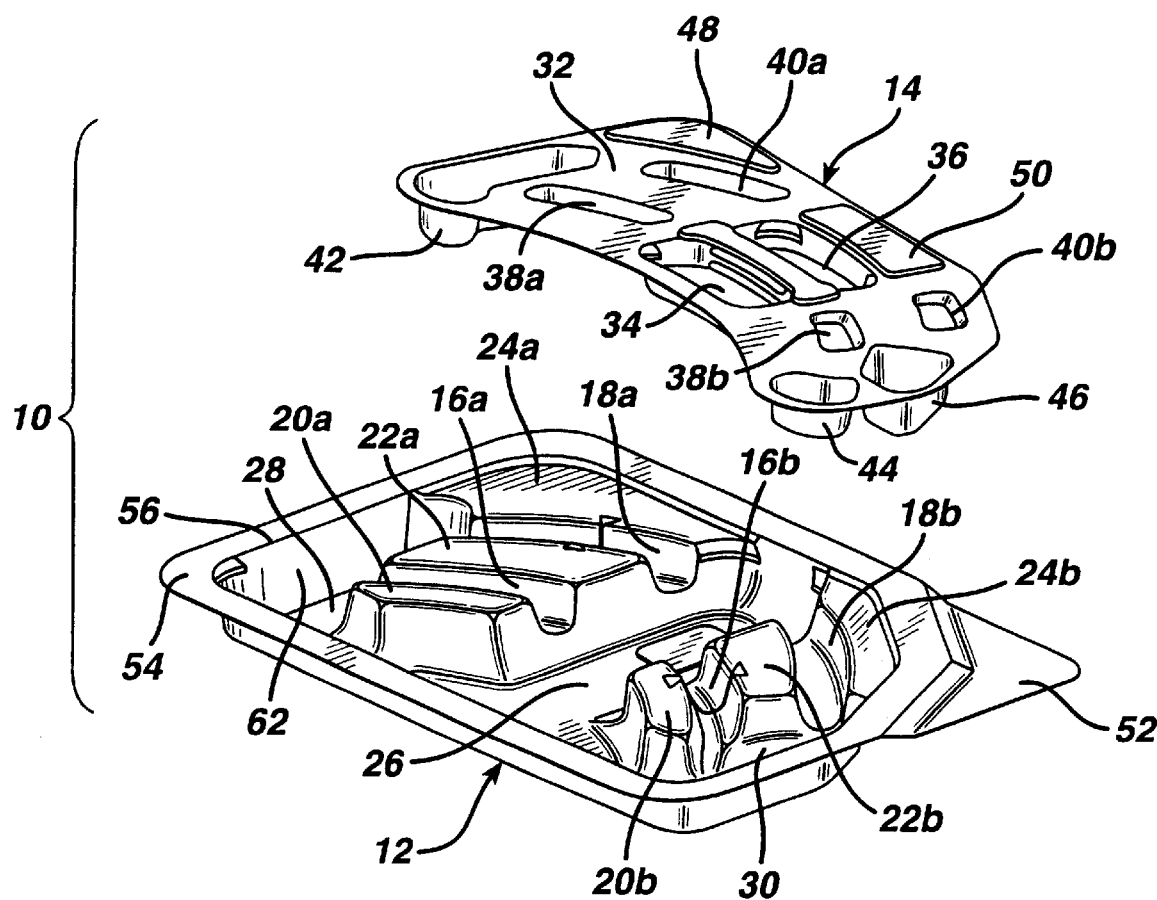
FIG. 1 is an exploded view of a needle package in accordance with an exemplary embodiment of the present invention.
Figure 2:
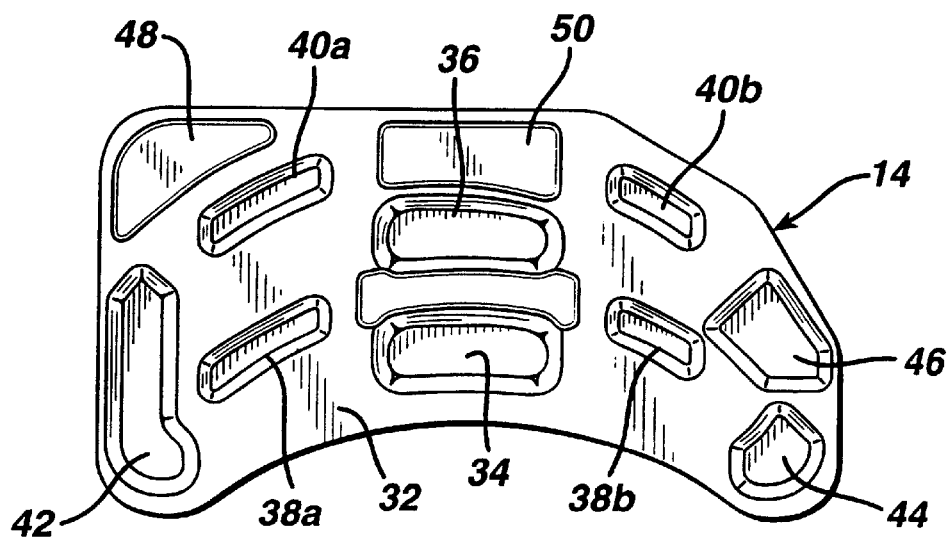
FIG. 2 is a plan view of a cover portion of the needle package of FIG. 1.
Figure 3:
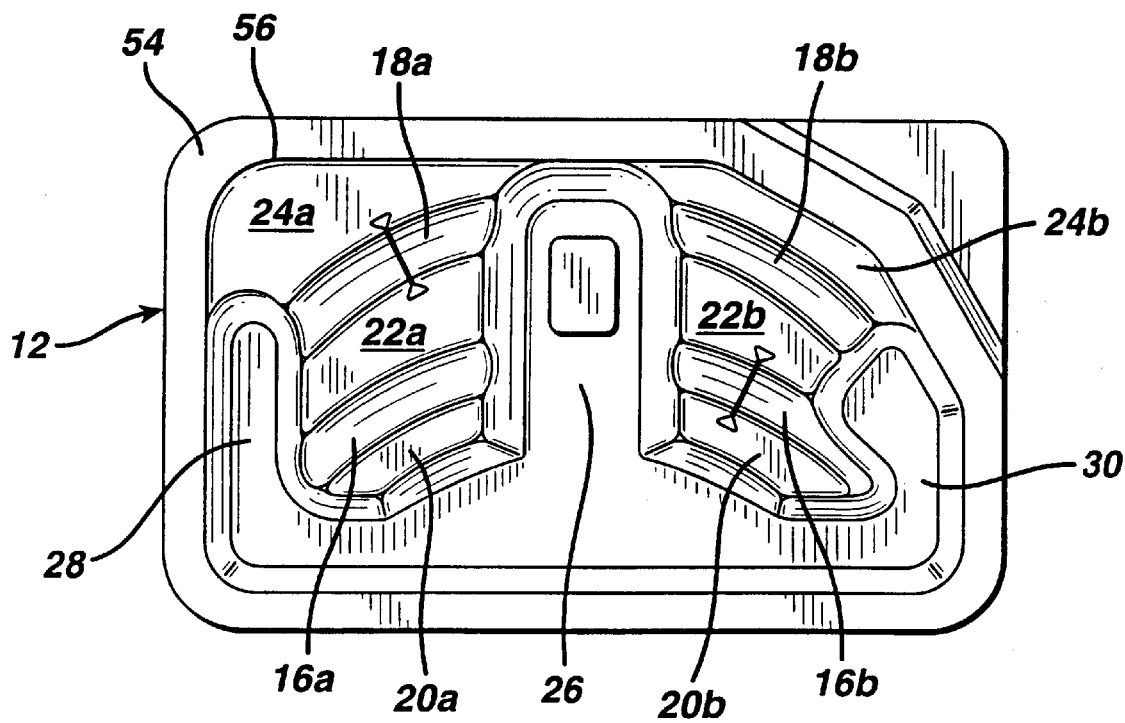
FIG. 3 is a plan view of a tray portion of the needle package of FIG. 1.

FIGS. 1–3 show a needle package 10 which is preferably thermoformed or injection molded from plastic, such as polypropylene, polystyrene, polyethylene and equivalents thereof to yield a "blister" type package. The needle package 10 has a tray portion 12 and a cover 14. The tray 12 has a plurality of needle channels 16a, 16b, 18a, 18b for receiving needles therein. The needle channels 16a, 16b and 18a, 18b are juxtaposed end-to-end to form an arcuate shape that may accommodate an arcuate needle extending through both, e.g., 16a, 16b. Alternatively, channels 16a, 16b could be straight for holding straight needles. A series of raised areas 20a, 20b, 22a, 22b, 24a and 24b define and separate the channels, 16a, 16b, 18a, 18b. A central recessed surface area 26 positioned between and below the channels 16a, 16b, 18a, 18b, facilitates a user in grasping needles that are present in the channels, e.g., 16a, 16b. A left recessed surface area 28 is provided at one end of the channels 16a, 18a and a right recessed surface area 30 is provided at a distal end of channels 16b, 18b.

The cover 14 has a substantially flat panel 32 into which is formed a pair of gripping recesses 34, 36, two pairs of needle abutments 38a, 38b and 40a, 40b, and three end stops or point guards 42, 44, 46. The flat panel 32 functions as a support member for end stops 42, 44, 46 and may be perforated to decrease material usage. The gripping recesses 34, 36 are positioned and dimensioned to be received proximate the central recessed area 26 and are intended to accommodate the fingers and thumb of a user to aid in grasping and removing the cover 14 from a position covering the tray 12. The gripping recesses 34, 36 may be disposed on the cover 14 in a position offset from the channels 16a, 16b, 18a, 18b. In this manner, the gripping recesses can extend down further toward the central recessed surface area 26 without interfering with the needles stored in the package 10. The needle abutments 38a, 38b and 40a, 40b are aligned with the channels 16a, 16b and 18a, 18b, respectively, extending downward towards the channels 16a, 16b, 18a, 18b and any needles contained therein to a selected extent for the purpose of constraining the upward motion of any needles contained in the package 10 to a selected degree. End stop 42 is shaped and positioned to be received proximate left recessed surface area 28 and end stops 44 and 46 are received proximate right recessed surface area 30 when the cover 14 is placed on the tray 12 after the needles have been loaded into the tray 12. When so placed, end stop 42 extends across channels 16a and 18a proximate left recessed surface area 28 and end stops 44 and 46 block channels 16b and 18b proximate right recessed surface area 30. The purpose of this juxtapositioning shall be explained below.

Tray 12 has a peripheral glue flange 54 for receiving a sealing membrane 60 (See FIG. 6) formed from aluminum, Tyvek or other conventional covering material used on blister packages which such sheet is adhered to the glue flange 54 by adhesive or plastic welding. An inner edge 56 of the glue flange 54 defines an inner peripheral shape that approximates the outer peripheral shape of the cover 14. A peripheral sidewall 62 extends between the recessed surface areas 26, 28, 30 to the inner edge 56 of glue flange 54.

Figure 4:
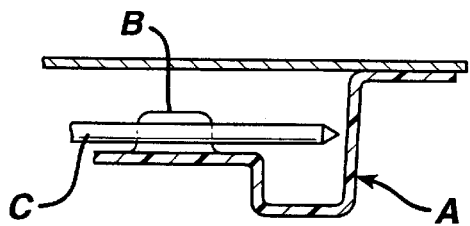
FIGS. 4 and 5 are diagrammatic views of a needle package in accordance with the prior art.
Figure 5:
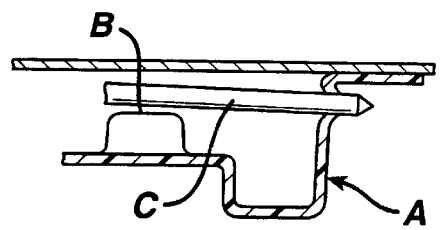

FIGS. 4 and 5 illustrate a prior art needle package having a needle retainer B for holding a needle C. In transit or during handling, the needle C can be displaced from the retainer B and pierce the wall of the package A.

Figure 6:
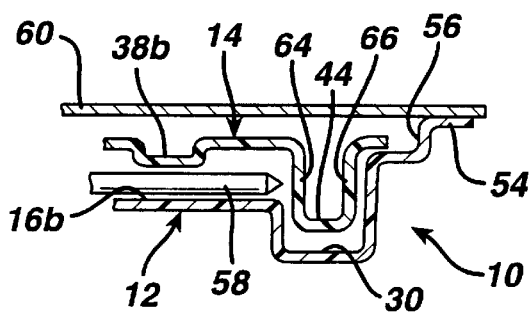
FIGS. 6 and 7 are diagrammatic views of the needle package of FIG. 1.
Figure 7:
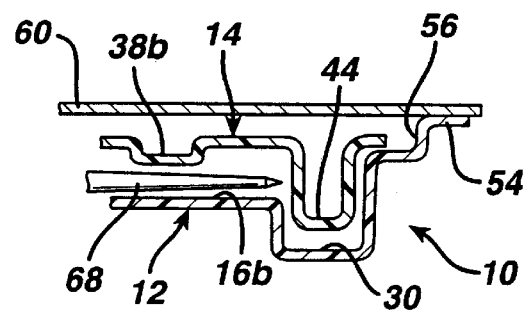

FIGS. 6 and 7 diagrammatically illustrate a portion of a needle package 10 in accordance with the present invention for holding a needle 58 and having a tray 12 with a recessed surface area 30. The needle 58 is received in a channel 16b. A cover 14 includes a needle abutment 38b for restraining the upward movement of the needle 58 and an end stop 44 which inserts into the recess 30. The tray 12 and cover 14 are covered by a sealing membrane 60 adhered to glue flange 54, such that the sealing membrane 60 prevents the cover from lifting away from the tray and allowing the end stop 44 to escape from the recess 30. In this manner, the end stop 44 is held in front of the needle 58 despite there being some clearance between the cover 14, the tray 12 and the sealing membrane 60. In order for the needle to penetrate the tray 12, it must first penetrate the end stop 44 which is defined by descending and ascending walls 64, 66 respectively, an unlikely occurrence. As can appreciated from FIG. 7, the fact that there is some clearance between the components of the package 10, e.g., between tray 12 and cover 14 and between cover 14 and sealing membrane 60 and because there is no requirement for an interference fit between the needle 68 and the package 10, needles of various sizes and shapes can be accommodated therein.

FIG. 7 depicts a tapered needle 68 in place of the straight needle 58 shown in FIG. 6. The loose fit between the tray 12 and the cover 14 permits the cover 14 to be easily withdrawn from the tray 12 to access the needle(s) contained therein. After the cover 14 is removed from the tray 12, the needle(s) contained therein can be easily removed by grasping them with the fingers since there is no frictional restraint to overcome. If desired, the tray 12 can be inverted over the sterile field to permit the needle(s) contained therein to be emptied from the tray 12 onto the sterile field.

It should be understood that the embodiments described herein are merely exemplary and that a person skilled in the art may make many variations and modifications without departing from the spirit and scope of the invention as defined in the appended claims.

We claim:

1. A package for holding a pointed object, comprising:

(a) a tray portion having an internal hollow delimited by a bottom surface and a sidewall, said internal hollow receiving the pointed object therein, said bottom surface having an object supporting portion that is elevated above a remainder thereof, the pointed object being supported upon said object supporting portion, said object supporting portion terminating at one end thereof in a descending wall that traverses from a level of said object supporting portion to a level of said remainder of said bottom surface, the point of the pointed object being positionable proximate said descending wall;

(b) a removable cover extending substantially parallel to said bottom surface over said internal hollow; and (c) a point guard depending from said cover towards said tray proximate said sidewall, said point guard interposed between said sidewall and a point on the pointed object to be held, said point guard extending parallel to said descending wall towards said remainder of said bottom surface to a level below said object supporting surface.

2. A package for holding a pointed object, comprising:

(a) a tray portion having an internal hollow delimited by a bottom surface and a sidewall, said internal hollow receiving the pointed object therein, said bottom surface having an object supporting portion elevated above a remainder thereof, the pointed object being supported upon said object supporting portion, said object supporting portion terminating at one end thereof in a descending wall that traverses from a level of said object supporting portion to a level of said remainder of said bottom surface, the point of the pointed object being positionable proximate said descending wall;

(b) a removable cover extending substantially parallel to said bottom surface over said internal hollow;

(c) a point guard depending from said cover towards said tray proximate said sidewall, said point guard interposed between said sidewall and a point on the pointed object to be held, said point guard extending parallel to said descending wall towards said remainder of said bottom surface to a level below said object supporting surface; and (d) a cover sheet extending over said tray portion covering said internal hollow, said cover and said pointed object, said cover sheet retaining said cover in a position wherein said point guard is interposed between said sidewall and the point of the pointed object.

3. The package of claim 2, wherein said descending wall, said remainder of said bottom surface and said sidewall define a first depressed area in said tray portion disposed proximate a first end of said object support surface and said point guard has a complementary shape to said first depressed area, such that said point guard inserts within said first depressed area.

4. The package of claim 3, wherein said point guard has a first wall section disposed proximate said object support surface and a second wall section disposed proximate said sidewall, said first wall section and said second wall section having a spacing therebetween, such that the point of the pointed object would penetrate said first wall section and said second wall section before penetrating said sidewall.

5. The package of claim 4, wherein said cover has a generally planar portion from which said point guard depends, said planar portion and said point guard covering said hollow.

6. The package of claim 5, further comprising a plurality of point guards, the pointed object having at least two points, a first point guard of said plurality being positioned proximate a first point of the pointed object and a second point guard of said plurality being positioned proximate a second point of the pointed object.

7. The package of claim 6, wherein said tray has a plurality of depressed areas, said first depressed area accommodating said first point guard and a second depressed area accommodating the second point guard.

8. The package of claim 7, further comprising a third depressed area located toward a center of said package, said third depressed area facilitating grasping the pointed object held within said package, said object support surface holding the object above a bottom surface of said third depressed area.

9. The package of claim 6, wherein said object support surface is in the form of a channel having a U-shaped cross-section.

10. The package of claim 9, wherein said channel is curved to accommodate a curved needle.

11. The package of claim 9, wherein said object support surface includes a plurality of channels with a U-shaped cross section, each of said channels accommodating at least one of the pointed objects.

12. The package of claim 2, wherein a clearance exists between said tray, said cover and said point guard, such that a range of differently dimensioned pointed objects can be contained in said package.

13. The package of claim 2, wherein said cover has object restraint projections projecting downwards in the same general direction as said point guard, said object restraint projections protruding into said channel to constrain the motion of the pointed object contained therein.

14. The package of claim 2, wherein said tray portion has a peripheral ledge to accommodate said cover, said cover having a peripheral shape that is complementary to the peripheral shape of said tray portion.

15. The package of claim 2, wherein said tray portion is of a thermoformed blister-type construction.

16. The package of claim 15, wherein said cover and said point guard are of thermoformed blister-type construction.

17. A package for a pointed object, comprising:
   (a) a tray portion having an internal hollow to receive the pointed object;
   (b) removable lid means, loosely fitting over said internal hollow of said tray portion and having means for preventing the pointed object from penetrating said tray portion depending therefrom;
   (c) object positioning means for positioning the pointed object relative to said preventing means; and
   (d) removable cover means for retaining the pointed object, said lid means and said preventing means being positioned on said tray with said preventing means in juxtaposition relative to the pointed object, said tray portion and said lid means being of thermoformed blister-type construction and wherein said tray portion, said lid means and said preventing means being dimensioned relative to one another such that the pointed object may have a range of dimensions.

\* \* \* \* \*